(12) United States Patent
Cowan et al.

(10) Patent No.: US 7,662,803 B2
(45) Date of Patent: Feb. 16, 2010

(54) METHOD FOR TREATING WARM-BLOODED VERTEBRATES WITH HALIDE-FREE GLUCOSAMINE-ACIDIC DRUG COMPLEXES

(75) Inventors: Alan Cowan, Ambler, PA (US); Robert B. Raffa, Norristown, PA (US); Ronald J. Tallarida, Mantua, NJ (US)

(73) Assignee: Gluconova, LLC, Wilmington, DE (US)

( * ) Notice: Subject to any disclaimer, the term of this patent is extended or adjusted under 35 U.S.C. 154(b) by 42 days.

(21) Appl. No.: 11/731,600

(22) Filed: Mar. 31, 2007

(65) Prior Publication Data

US 2007/0248660 A1 Oct. 25, 2007

Related U.S. Application Data

(63) Continuation-in-part of application No. 11/223,295, filed on Sep. 9, 2005.

(60) Provisional application No. 60/611,211, filed on Sep. 17, 2004.

(51) Int. Cl.
*A01N 43/04* (2006.01)
*A01N 43/08* (2006.01)
*C07H 5/04* (2006.01)
*C07H 5/06* (2006.01)
*C07H 17/04* (2006.01)

(52) U.S. Cl. .............. 514/62; 536/55.2; 536/17.2

(58) Field of Classification Search ............... None
See application file for complete search history.

(56) References Cited

U.S. PATENT DOCUMENTS

| | | | | |
|---|---|---|---|---|
| 3,008,874 | A | 11/1961 | Feeney et al. ............ 167/55 |
| 4,748,174 | A | 5/1988 | Veronesi ............... 514/226.5 |
| 4,877,620 | A | 10/1989 | Loew et al. ............. 424/451 |
| 5,028,625 | A | 7/1991 | Motola et al. ........... 514/557 |
| 5,604,206 | A | 2/1997 | Paradies ................. 514/23 |
| 6,291,527 | B1 | 9/2001 | Giorgetti ................ 514/570 |
| 6,294,520 | B1 * | 9/2001 | Naito .................... 514/23 |
| 6,486,307 | B1 | 11/2002 | Gandhi et al. ............ 536/20 |
| 6,608,041 | B2 | 8/2003 | Hammerly ............... 514/54 |
| 6,900,189 | B2 * | 5/2005 | Raffa et al. ............. 514/62 |
| 2002/0058642 | A1 | 5/2002 | Raffa et al. ............. 514/62 |
| 2003/0119761 | A1 * | 6/2003 | Christian ............... 514/42 |
| 2003/0148998 | A1 | 8/2003 | Fan et al. |
| 2003/0181419 | A1 * | 9/2003 | Hwang et al. ............ 514/62 |
| 2004/0077055 | A1 | 4/2004 | Fosdick et al. .......... 435/85 |
| 2004/0091976 | A1 | 5/2004 | Deng et al. ............. 435/84 |
| 2005/0148545 | A1 | 7/2005 | Fosdick et al. .......... 514/62 |
| 2005/0148546 | A1 | 7/2005 | Grund et al. ............ 514/62 |

OTHER PUBLICATIONS

Drug Development and Industrial Pharmacy, 25(8), 967-972 (1999).

* cited by examiner

*Primary Examiner*—Ardin Marschel
*Assistant Examiner*—Amy A Lewis
(74) *Attorney, Agent, or Firm*—Jack Matalon

(57) ABSTRACT

A method of treating a warm-blood vertebrate. The vertebrate may be a human being or a lower animal. The treatment method involves administering to the vertebrate in need of such treatment a pharmaceutically effective amount of a complex of halide-free glucosamine and a therapeutic drug having a $pK_a$ of less than 7. Preferably, the complex is stabilized by coating it with at least one pharmaceutically acceptable polymer comprising a water-soluble, water-immiscible and/or water-swellable homopolymer and/or copolymer. Suitable polymers include carboxypolymethylene homopolymers and copolymers; polyethylene glycol homopolymers and copolymers, povidone homopolymers and copolymers, polyacrylic acid homopolymers and copolymers; polyacrylamide homopolymers and copolymers; polysaccharides; and mixtures of two or more of the foregoing polymers. The resultant polymer-coated complex will be stable upon exposure to ambient temperature and/or the atmosphere. Suitable acidic therapeutic drugs may be found in one or more of the following classes of therapeutic drugs: α- and β-Adrenergic Agonists; Narcotic and Non-Narcotic Analgesics; Anorexics; Antiallergics; Antianginals; Antiarrhythmics; Antiasthmatics; Antibiotics; Anti-coagulants; Anticonvulsants; Antidepressants; Antidiabetics; Antihistaminics; Anti-hypertensives; Nonsteroidal Anti-Inflammatories; Antimigraines; Antineoplastics; Antiparkinsonians; Antipsychotics; Antipyretics; Antispasmodics; Antithrombotics; Anti-ulceratives; Anxiolytics; Decongestants; Diuretics; Hepatoprotectants; Sedatives; and Vasodilators.

20 Claims, No Drawings

US 7,662,803 B2

METHOD FOR TREATING WARM-BLOODED VERTEBRATES WITH HALIDE-FREE GLUCOSAMINE-ACIDIC DRUG COMPLEXES

CROSS-REFERENCE TO RELATED APPLICATION

This application is a continuation-in-part of application Ser. No. 11/223,295 filed Sep. 9, 2005, which in turn claimed the benefit of provisional application Ser. No. 60/611,211 filed Sep. 17, 2004.

FIELD OF THE INVENTION

The invention relates to a method for treating warm-blooded vertebrates, i.e., human beings and lower animals, with complexes of halide-free glucosamine and acidic drugs.

BACKGROUND OF THE INVENTION

Glucosamine is a well-known amino monosaccharide found in chitin, glycoproteins and glycosaminoglycans. Glucosamine is widely used for the treatment of rheumatic fever, arthritic and arthosic complaints, in the acute as well as chronic forms, as well as in the treatment of pathological conditions originating from metabolic disorders of the osteoarticular tissue. Although products in the marketplace are labeled as, or referred to as, "glucosamine", they are misnomers since such products consist of glucosamine hydrochloride or as unreacted mixtures of glucosamine hydrochloride and a salt such as potassium or sodium sulfate.

One drawback of many therapeutic drugs is their relative insolubility in the body after they have been administered to a patient. It would be most desirable if more soluble versions of therapeutic drugs could be made available.

It has now been found that complexes of halide-free glucosamine and acidic drugs are more soluble than the drugs themselves. An added benefit is that glucosamine itself is formed in the body (typically in the form of glucosamine phosphate) and therefore no "foreign" ingredients will be introduced in the body when the complexes employed in the treatment method of the invention are administered to warm-blooded vertebrates.

Salts or mixtures of "glucosamine" or "glucosamine sulfate" and a therapeutic drug such as aspirin, ibuprofen, ketoprofen are known in the prior art, e.g., see U.S. Patent Publication 2002/0058642 A1; U.S. Pat. No. 6,608,041 B2; U.S. Pat. No. 6,291,527 B1; U.S. Pat. No. 5,604,206; and U.S. Pat. No. 3,008,874. However, the "glucosamine" or "glucosamine sulfate" employed in such compositions are misnomers, inasmuch as such materials are actually glucosamine hydrochloride or mixed salts of glucosamine hydrochloride and an alkali or alkaline earth metal sulfate.

In contradistinction thereto, the glucosamine employed in preparing the complexes employed in the method of the invention is halide free and as a result, the complexes will contain neither a halide nor any extraneous sulfate salts nor any extraneous cations (e.g., sodium, potassium, calcium, etc.).

DETAILS OF THE INVENTION

The invention pertains to a method for treating warm-blooded vertebrates. The method involves the administration to the vertebrate of a pharmaceutically effective amount of a complex of halide-free glucosamine and an acidic drug, i.e., a therapeutic drug having a $pK_a$ of less than 7 (such drugs will contain one or more acidic functionalities such as a carbonyl moiety, a carboxyl moiety, a sulfoxide moiety, etc.)

Descriptions of such complexes and the methods of preparation thereof appear in patent application Ser. No. 11/223,686, filed Sep. 9, 2005. The disclosure of the foregoing co-pending patent application is incorporated herein in its entirety by reference.

Glucosamine, extracted from shellfish or prepared by a fermentation process, is only available in the form of its hydrochloride salt. If the glucosamine hydrochloride salt is neutralized with a base, e.g., NaOH, KOH, etc. in order to release the glucosamine, the resultant product will always contain a salt, i.e., NaCl or KCl, respectively, and it is not possible to separate the glucosamine from the salt since both the glucosamine and the salt are fully soluble in water.

Free glucosamine may be prepared by the method recited in *Chem. Ber.*, volume 75, page 1274. Such method involves the treatment of glucosamine hydrochloride with an ethanolic solution of a tertiary base such as triethylamine. Triethylamine hydrochloride is filtered off and the free glucosamine is then recovered from the reaction mixture. However, triethylamine is a toxic material even in small quantities and the yield of the free glucosamine is quite low. Moreover, the free glucosamine still contains residual chloride.

A method for producing halide-free glucosamine with a very high degree of purity has now been discovered. Such method is fully described in co-pending patent application Ser. No. 11/223,236 filed Sep. 9, 2005. The aforesaid co-pending patent application is hereby incorporated herein in its entirety. By way of summary, the method disclosed in the aforesaid co-pending patent application is as follows:

(a) a glucosamine halide complex (e.g., glucosamine hydrochloride, glucosamine hydroiodide, etc.) is reacted with a lithium base in the presence of a $C_1$-$C_4$ alcohol to thereby generate a $C_1$-$C_4$ alcohol solution of a lithium halide and insoluble halide-free glucosamine; and (b) the insoluble halide-free glucosamine is separated from the $C_1$-$C_4$ alcohol solution of the lithium halide complex.

For maximum yields, the reaction should be carried out at a temperature of about 15 to about 35° C.; conveniently, the reaction may be carried out at ambient temperatures. The $C_1$-$C_4$ alcohol may be, e.g., methanol, ethanol (preferably anhydrous), isopropanol, etc; the preferred alcohol comprises methanol. The lithium base may be anhydrous lithium hydroxide, lithium hydroxide monohydrate, lithium methoxide, lithium ethoxide or lithium isopropoxide. The preferred lithium base comprises anhydrous lithium hydroxide. It has been found that the presence of water in the reaction mixture reduces the yield of the halide-free glucosamine. Accordingly, it is preferred that the reaction be carried out under anhydrous conditions. In general, the lithium base is employed in an amount of about 1.0 to about 1.2 moles per mole of halide present in the glucosamine halide complex. Excess lithium base is unnecessarily wasteful and will reduce the yield of the halide-free glucosamine. Typically, the alcohol is employed in an amount of about 1 to about 10 parts, preferably 3 to 6 parts, per part of lithium base.

After allowing the reaction to proceed (preferably with stirring) for about 5 minutes to about 2 hours, the solid halide-free glucosamine is filtered off from the resultant alcohol solution of the lithium halide and washed with additional alcohol. The halide-free glucosamine may then be dried under vacuum at a temperature of about 15 to about 30° C. The yield typically ranges from about 85 to about 90%. The halide-free glucosamine is quite pure. It will have a purity level of greater than about 99 wt. % and the halide content will be about 0.01 wt. % or less, e.g., 100 ppm or less and very often, the halide content will be less than 50 ppm and as low as 25 ppm. Based upon the residual halide content of the halide-free glucosamine, the lithium residue in the glucosamine will generally be about 20 ppm or less and very often, the lithium residue content will be less than 10 ppm The halide-free glucosamine is quite hygroscopic and will decompose over a period of time if subjected to ambient temperature and/or to the atmosphere. Accordingly, it should be refrigerated in a closed container or preferably promptly, used after recovery for conversion to the complexes of the invention as described below.

The halide-free glucosamine may be readily converted to the glucosamine-acidic drug complex of the invention by reacting the glucosamine with a therapeutic drug having at least one acidic functionality, i.e. a therapeutic drug having a $pK_a$ of less than 7. The molar ratio of the halide-free glucosamine to the acidic drug in the complex is not critical and may be in the range of about 1 mole of glucosamine per mole of the drug up to about 15 moles of the glucosamine per mole of the drug. If the selected drug has more than one acidic functionality, the molar ratio of the glucosamine to the selected drug should be adjusted such that there will be about 1 to about 15 moles of glucosamine employed per acidic functionality in the selected drug.

Typically, the reaction mixture will comprise the halide-free glucosamine, about 5 to about 30 parts, preferably 15 to 20 parts, of water (preferably purified water) per part of the glucosamine and the selected drug. Although lesser amounts of water may be employed, the resultant solutions may become too viscous to be properly agitated, particularly if the glucosamine-therapeutic drug complex is not isolated from the reaction mixture, but is stabilized by the addition of a polymer to the reaction mixture, as described below. On the other hand, excessive amounts of water may lead to reduced yields if a water-miscible solvent is used to recover the complex and if freeze-drying is used to recover the complex, the freeze-drying process becomes more time-consuming and expensive because of the large amount of water to be removed from the reaction mixture.

The selected acidic drug is slowly added to the aqueous solution of the halide-free glucosamine while the aqueous solution is agitated, e.g. over a period of a few minutes, and the reaction mixture is further agitated for 5 to 120 minutes. The reaction is typically conducted at a temperature of about 15 to about 40° C. Thereafter, the glucosamine-acidic drug complex of the invention may be recovered from the reaction mixture by freeze-drying or by adding a water-miscible solvent such as acetone to the reaction mixture such that the complex will precipitate from the reaction mixture and the complex is then recovered by conventional filtration methods. The complex may then be dried by conventional methods, e.g., a stream of nitrogen, a vacuum oven at 30-50° C. for a period of 1 to 10 hours, etc. It is preferred that the recovery of the halide-free glucosamine-acidic drug complex of the invention be carried out by a freeze-drying process as described in greater detail below.

Some of the halide-free glucosamine-acidic drug complexes of the invention may decompose over a period of time if they are exposed to ambient temperatures or the atmosphere. Therefore, it is preferred that the complex not be recovered from the reaction mixture as is, but converted to a stabilized form prior to recovery. Conversion of the complex to its stabilized form may be desirable even for those complexes that do not decompose upon exposure to ambient temperatures and/or the atmosphere, since the pharmaceutically acceptable polymers employed in stabilizing, i.e., coating, the complexes of the invention may provide extended-release properties when the complexes are administered to warm-blooded vertebrates in need of treatment.

Stabilization of the halide-free glucosamine-acidic drug complex is readily accomplished by adding a suitable pharmaceutically acceptable polymer to the reaction mixture prior to recovery of the complex. The pharmaceutically acceptable polymer may be a water-soluble, water-dispersible and/or or a water-swellable homopolymer and/or copolymer. Preferably, the pharmaceutically acceptable polymer will be water-soluble. In general, the polymer will be employed in an amount of about 2 to about 70, preferably 20 to 50, parts by weight of the polymer per part of the complex in the reaction mixture.

Nonlimiting examples of commercially available pharmaceutically acceptable homopolymers and copolymers suitable for stabilizing the halide-free glucosamine-therapeutic drug complexes of the invention include the following: carboxypoly-methylene homopolymers and copolymers, i.e., vinyl polymers having active carboxyl groups such as high molecular weight homopolymers of acrylic acid crosslinked with allylsucrose or allylpentaerythritol and copolymers of acrylic acid modified by long chain ($C_{10}$-$C_{30}$) alkyl acrylates and crosslinked with allylpentaerythritol—such polymers are commercially available and are marketed as Carbopol® polymers; polyethylene glycol homopolymers and copolymers (e.g., polyethylene-co-lactic acid copolymers), particularly polyethylene glycol polymers having molecular weights in the range of about 2,000 to about 20,000, preferably 4,000 to 18,000; polypropylene glycol homopolymers and copolymers, especially polypropylene glycol homopolymers having molecular weights of about 800 to about 18,000; ethylcellulose; povidone homopolymers, i.e., synthetic water-soluble homopolymers of N-vinyl-pyrrolidone, especially those having a molecular weight of about 2,500 to about 10,000; copovidone, i.e. synthetic random copolymers of N-vinylpyrrolidone and vinyl acetate in a 60:40 ratio; polyacrylic acid homopolymers and copolymers; polyacrylamide homopolymers and copolymers; polysaccharides; etc.

The choice of particular homopolymers and/or copolymers for coating, i.e., stabilizing, the complex, is not critical so long as the polymers are pharmaceutically acceptable, have the capability of coating, i.e., stabilizing, the complex without any adverse chemical reaction occurring between the selected polymer and the complex and the resultant coated complexes are stable, i.e., they will not undergo decomposition when exposed to ambient temperatures and/or the atmosphere.

If the complex is to be recovered from the reaction mixture in a stabilized form, the desired pharmaceutically acceptable polymer is added, preferably in increments, with stirring, to the aqueous halide-free glucosamine solution preferably prior to the addition of the acidic drug. This step will generally take about 5 to about 15 minutes and is preferably conducted at a temperature of about 15 to about 40° C. After all increments of the selected polymer have been added, stirring is continued for an additional 5 to 120 minutes. Thereafter, the acidic drug is slowly added to the reaction mixture, while maintaining the reaction mixture at a temperature of about 15 to 40° C.

The last step is the recovery of the polymer-coated, i.e., stabilized, complex from the reaction mixture. The stabilized complex may be recovered from the reaction mixture by freeze-drying or by adding a water-miscible solvent, e.g., acetone, to the reaction mixture to cause the stabilized complex to precipitate out from the reaction mixture. The precipitate is then recovered by conventional filtration methods and it may be dried as described below. Of course, the choice of stabilizing polymer and water-miscible solvent should be such that the polymer will not dissolve in, or otherwise react with, the solvent.

The complex of the invention is preferably recovered by removal of water from the reaction mixture by freeze-drying, a well-known technique for removing water from compositions. Although freeze-drying is a time-consuming process, (a reaction mixture containing one liter of water will typically require 30-36 hours to remove about 97% of the water), it is preferred since the formation of decomposition products resulting from heating the reaction mixture or adding solvents to the reaction mixture can be avoided.

The freeze-drying process will generally be carried out at a reduced pressure and reduced temperature, e.g., a pressure of not greater than 500 milliTorre, preferably 300 to 100 milliTorre and at a temperature of about −60 to about −20° C., preferably −50 to −40° C. The endpoint of the completion of the freeze-drying process may be determined by condensing and measuring the quantity of water removed during the freeze-drying process. The time required for completion of the freeze-drying process will vary depending on factors such as pressure, temperature, quantity of reaction mixture to be free-dried, level of water to be tolerated in the stabilized halide-free glucosamine-drug complex, the thickness and surface area of the reaction mixture in the trays of the freeze-drying equipment, etc.

If the stabilized complex is to be recovered by precipitation from the reaction mixture by addition of a water-miscible solvent such as acetone to the reaction mixture, generally about 2 to about 10 parts of solvent per part of reaction mixture will be required.

After the stabilized complex has been recovered from the reaction mixture, it may be dried by conventional techniques, e.g., a stream of nitrogen, vacuum oven at a temperature of about 30 to about 50° C. for 1 to 10 hours or more, etc.

It should also be noted that the stabilization of the complexes of the invention may provide an additional advantage to warm-blooded vertebrates to whom such complexes are administered. The stabilized, i.e., polymer-coated, versions of the complexes may provide extended release properties, i.e., the glucosamine-therapeutic drug complex may be released within the vertebrate over an extended period of time, thereby possibly resulting in a reduction of the frequency and the amount of the dosage that would otherwise be required to be administered to the vertebrate.

The therapeutic drug that is to be complexed with the halide-free glucosamine may be any therapeutic drug that exhibits an acidic $pK_a$, i.e., a $pK_a$ of less than 7.0. Such drugs will contain one or more acidic functionalities such as a carbonyl moiety, a carboxyl moiety, a sulfoxide moiety, etc. The list of therapeutic drugs that fit such definition is quite voluminous. Suitable therapeutic drugs containing at least one acidic functionality may be found in one or more of the following nonlimiting, representative classes of drugs: α- and β-Adrenergic Agonists; Narcotic and Non-Narcotic Analgesics, Anorexics; Antiallergics; Antianginals; Antiarrhythmics; Antiasthmatics; Antibiotics; Anti-coagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives, Anxiolytics; Decongestants; Diuretics; Hepatoprotectants; Sedatives; and Vasodilators.

Not every possible therapeutic drug within the foregoing-listed classes will be suitable for preparing a complex with the halide-free glucosamine. Only those therapeutic drugs that are sufficiently acidic in nature to form such a complex with the halide-free glucosamine are suitable. As mentioned above, such therapeutic drugs will have a $pK_a$ of less than 7.0 and will contain at least one acid functionality, e.g. a carbonyl moiety, a carboxyl moiety, a sulfoxide moiety, etc.

Particularly suitable specific drugs within the foregoing classes include: acetaminophen, acetazolamide, ampicillin, ampiroxicam, aspirin, bromfenac, carprofen, celecoxib, cetirizine, chlorothiazide, chlorpropamide, ciprofloxacin, diazepam, diclofenac, ethacrynic acid, flufenamic acid, furosemide, ibuprofen, indomethacin, indoprofen, ketoprofen, levodopa, meelofenamic acid, methotrexate, methyldopa, naproxen, orazamide, penicillamine, pentobarbital, phenobarbital, phenytoin, piroxicam, propylthiouracil, protoporphyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof.

The treatment method of the invention involves the administration of a pharmaceutically effective amount of one or more of the complexes to a warm-blooded vertebrate in need of such treatment. It should be understood that the term "warm-blooded vertebrate" is intended to encompass human beings as well as lower animals, e.g., dogs, cats, horses, cattle, swine, poultry, etc.

The pharmaceutically effective amount of the complex of the glucosamine and an acidic therapeutic drug may be administered to the warm-blooded vertebrate in need of such treatment by one or more of a variety of conventional methods, e.g., orally, buccally, intravenously, intramuscularly, parenterally, subcutaneously, sublingually, topically, etc. The complexes employed in the treatment method of the invention may be utilized in the form of tablets, caplets, granules, powder, capsules, spansules, gel caps, solutions, suspensions, syrups, mouthwashes, salves, foams, gels, creams, vaginal bougies, suppositories, and the like.

The following nonlimiting examples shall serve to illustrate the preferred embodiments of the invention. Unless otherwise indicated, all parts and percentages are on a weight basis. In each of the examples, the complexes were furnished by JFC Technologies, LLC, Bound Brook, N.J. (the assignee of patent application Ser. No. 223,686, filed Sep. 9, 2005). The complexes were prepared in accordance with the teachings of the aforesaid co-ending application that is incorporated herein in its entirety by reference and consisted of halide-free glucosamine complexed with the indicated acidic therapeutic drug in a ~1:1 molar ratio.

EXAMPLE 1

Test for Analgesia

The test that was employed is an abdominal irritant test that was carried out in accordance with the procedure set forth by Collier et al., *Brit. J. Pharmacol.*, 32:295-310 (1968).

Each group of 10 male Swiss-Webster mice weighing 25-30 g received an oral injection of (a) distilled water or 1% Tween® 80; or (b) a previously established analgesic dose of either ibuprofen (30 mg/kg), ketoprofen (200 mg/kg), naproxen (30 mg/kg), piroxicam (3 mg/kg) or aspirin (150 mg/kg) or (c) a halide-free glucosamine complex of either ibuprofen (30 mg/kg of the complex), ketoprofen (200 mg/kg of the complex), naproxen (30 mg/kg of the complex), piroxicam (3 mg/kg of the complex) or aspirin (150 mg/kg of the complex).

It was noted that the halide-free glucosamine complexes of ibuprofen, ketoprofen, naproxen, piroxicam and aspirin were all 100% soluble in distilled water in contrast to the parent compounds which had to be suspended in water containing 1% Tween® 80.

Thirty minutes after each injection, each mouse was injected i.p. (0.25 ml/0.25 g) with an aqueous solution of acetylcholine bromide (5.5 mg/kg). The animals were then observed for 10 minutes for the presence or absence of a characteristic wave of contraction and elongation passing caudally along the abdominal wall, accompanied by a twisting of the trunk and followed by extension of the hind limbs. The percentage of analgesia was then calculated for each group based on the percentage of mice displaying no behavioral response.

The results of the abdominal irritant test were as follows:

At 30 mg/kg, both ibuprofen and the halide-free glucosamine complex of ibuprofen (containing 53% ibuprofen) provided 80% analgesia.

At 200 mg/kg, ketoprofen and the halide-free glucosamine complex of ketoprofen (containing 59% ketoprofen) provided 56% and 90% analgesia, respectively.

At 30 mg/kg, naproxen and the halide-free glucosamine complex of naproxen (containing 46% naproxen) provided 70% and 50% analgesia, respectively.

At 3 mg/kg; both piroxicam and the halide-free glucosamine complex of piroxicam (containing 65% piroxicam) provided 70% analgesia.

At 0.50 mg/kg, both aspirin and the halide-free glucosamine complex of aspirin (containing 50% aspirin) provided 70% analgesia.

Based on the above result, it is clear that the halide-free glucosamine complex of each non-steroidal anti-inflammatory drug was a more potent analgesic on a proportional content basis than the parent drug.

EXAMPLE 2

Elevated Plus Maze (Test for Antianxiety Activity)

The apparatus employed in this example consisted of two darkened enclose arms and two open arms, with a light beam focused on the open arms. The maze is elevated to a height of 55 cm. Mice have a desire to explore the apparatus, but the open, bristly lit arms present an aversive environment so that their preference is to remain in the enclosed arms. Standard antianxiety drugs such as diazepam help the animals to overcome this apprehension such that they spend more time than vehicle-injected controls exploring the open arms of the maze.

Groups of six male Swiss Webster mice (25-30 g) received an intraperitoneal injection of one of the following treatments: vehicle alone diazepam plus vehicle (0.50 mg/kg); halide-free glucosamine-diazepam complex, ~1:1 molar ratio, (0.50 mg/kg in water). Thirty minutes later, each animal was individually placed on the elevated maze for 5 minute and the time spent on the open (aversive) arms was recorded. The results are set forth in the table below. Note that the term "s.e.m." stands for the standard error of the mean (either side of the mean value) of the precision by which the mean is estimated.

| Antianxiety Activity in the Elevated Plus Maze | | | |
|---|---|---|---|
| Compound | Dose (mg/kg) | No. of mice | Mean time (sec) ± s.e.m. in open arms |
| Vehicle | — | 6 | 6.8 ± 3.9 |
| Diazepam | 0.50 | 6 | 30.3 ± 12.7 |
| Complex | 0.50 | 6 | 34.0 ± 13.6 |

Based on the results set forth in the above table, it was concluded that comparable antianxiety activity was demonstrated with both 0.5 mg/kg of diazepam and 0.50 mg/kg of the halide-free glucosamine-diazepam complex, notwithstanding that in the complex, the diazepam constituted only 61% of the complex. It was also observed that the halide-free glucosamine enhanced the water solubility of diazepam.

EXAMPLE 3

Metrazol-Induced Convulsions (Test for Antiepileptic Activity)

Three groups of 10 male Swiss Webster mice (25-30 g) received a subcutaneous injection of one of the following treatments: vehicle alone; phenytoin (15 mg/kg in 1% Tween® 80); halide-free glucosamine-phenytoin complex, ~1:1 molar ratio, (15 mg/kg in water). Fifteen minutes later, each animal was injected subcutaneously with a convulsant dose of metrazol (120 mg/kg) and observed for 60 minutes for an entire-body convulsion. The results are set forth in the table below.

| Anticonvulsant activity in the mouse metrazol test | | | |
|---|---|---|---|
| Compound | Dose(mg/kg) | No. of mice | No. of mice protected (no body seizures in 60 min.) |
| Vehicle | — | 10 | 0/10 |
| Phenytoin | 15 | 10 | 1/10 |
| Complex | 15 | 10 | 7/10 |

Based on the results set forth in the table above, it was concluded that significantly improved anticonvulsant activity was demonstrated for the complex over the non-complexed phenytoin notwithstanding that the phenytoin constituted only 60% of the complex. It was also observed that the halide free glucosamine enhanced the water solubility of phenytoin.

What is claimed is:

1. A method of treating a warm-blooded vertebrate comprising the steps of:
   (a) providing a complex of (i) glucosamine having a purity level of at least 99 wt. % and a maximum halide content of 0.01 wt. %, and (ii) a therapeutic drug having a $pK_a$ of less than 7; and
   (b) administering to the vertebrate in need of the treatment a pharmaceutically effective amount of such complex.

2. The method of claim 1 wherein the complex further comprises a pharmaceutically acceptable polymer.

3. The method of claim 2 wherein the polymer comprises a water-soluble, water-dispersible and/or a water-swellable homopolymer and/or copolymer.

4. The method of claim 2 wherein the polymer is selected from the group consisting of carboxypolymethylene homopolymers and copolymers; polyethylene glycol homopolymers and copolymers, povidone homopolymers and copolymers; polyacrylic acid homopolymers and copolymers; polyacrylamide homopolymers and copolymers; polysaccharides; and mixtures of two or more of the foregoing polymers.

5. The method of claim 1 wherein the therapeutic drug is selected from the group consisting of the classes of α- and β-Adrenergic Agonists; Adrenergic Agonists; Narcotic and Non-Narcotic Analgesics; Anorexics; Antiacne and Keratolytics; Antiallergics; Antianginals; Antiarrhythniics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives; Anxiolytics; Diuretics; Decongestants; Hepatoprotectants; Sedatives; and Vasodilators.

6. The method of claim 5 wherein the drug is selected from the group consisting of acetaminophen, acetazolamide, ampicillin, ampiroxicam, aspirin, bromfenac, carprofen, celecoxib, chiorothiazide, chiorpropamide, cetirizine, ciprofloxacin, diazepam, diclofenac, ethacrynic acid, flufenamic acid, flirosemide, ibuprofen, indomethacin, indoprofen, ketoprofen, levodopa, meclofenamic acid, methotrexate, methyldopa, naproxen, orazamide, penicillamine, pentobarbital, phenobarbital, phenytoin, piroxicam, propyithiouracil, protoprophyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof.

7. The method of claim 1 wherein the complex is administered to the vertebrate orally, buccally, intravenously, intramuscularly, parenterally, subcutaneously, sublingually and/or topically.

8. The method of claim 1 wherein the complex is utilized in the form of tablets, caplets, granules, powder, capsules, spansules, gel caps, solutions, suspensions, syrups, mouthwashes, salves, foams, gels, creams, vaginal bougies and/or suppositories.

9. The method of claim 1 wherein the glucosamine and the drug are present in the complex in a ratio of about 1 to about 15 moles of glucosamine per mole of the drug.

10. A method of treating a warm-blooded vertebrate comprising the steps of:
   (a) providing a pharmaceutically acceptable polymer-coated complex of glucosamine having a purity level of at least 99 wt. % and a maximum halide content of about 0.01 wt. %, and a therapeutic drug having a pKa of less than 7; and
   (b) administering a pharmaceutically effective amount of such polymer-coated complex vertebrate in need of the treatment.

11. The method of claim 10 wherein the pharmaceutically acceptable polymer comprises a water-soluble, water-dispersible and/or a water-swellable homopolymer and/or copolymer.

12. The method of claim 10 wherein the pharmaceutically acceptable polymer is selected from the group consisting of carboxypolymethylene homopolymers and copolymers; polyethylene glycol homopolymers and copolymers, povidone homopolymers and copolymers; polyacrylic acid homopolymers and copolymers; polyacrylamide homopolymers and copolymers; polysaccharides; and mixtures of two or more of the foregoing polymers.

13. The method of claim 10 wherein the therapeutic drug is selected from the group consisting of the classes of α- and β-Adrenergic Agonists; Narcotic and Non-Narcotic Analgesics; Anorexics; Antiacne and Keratolytics; Antiallergics; Antianginals; Antiarrhythmics; Antiasthmatics; Antibiotics; Anticoagulants; Anticonvulsants; Antidepressants; Antidiabetics; Antihistaminics; Antihypertensives; Nonsteroidal Anti-Inflammatories; Antimigraines; Antineoplastics; Antiparkinsonians; Antipsychotics; Antipyretics; Antispasmodics; Antithrombotics; Antiulceratives; Anxiolytics; Diuretics; Decongestants; Hepatoprotectants; Sedatives; and Vasodilators.

14. The method of claim 13 wherein the therapeutic drug is selected from the group consisting of acetaminophen, acetazolamide, ampicillin, ampiroxicam, aspirin, bromfenac, carprofen, celecoxib, cetirizine; chiorothiazide, chiorpropamide, ciprofloxacin, diazepam, diclofenac, ethacrynic acid, flufenamic acid, furosemide, ibuprofen, indomethacin, indoprofen, ketoprofen, levodopa, meclofenamic acid, methotrexate, methyldopa, naproxen, orazamide, penicillamine, pentobarbital, phenobarbital, phenytoin, piroxicam, propylthiouracil, protoprophyrin IX, rofecoxib, salicyclic acid, sulfadiazine, sulfapyridine, sulindac, theophylline, thioctic acid, timonacic, tiopronin, tolbutamide, tolfenamic acid, warfarin, tolmetin, zaltoprofen, and mixtures thereof.

15. The method of claim 10 wherein the pharmaceutically acceptable polymer-coated complex is administered to the vertebrate orally, buccally, intravenously, intramuscularly, parenterally, subcutaneously, sublingually and/or topically.

16. The method of claim 10 wherein the pharmaceutically acceptable polymer-coated complex is utilized in the form of tablets, caplets, granules, powder, capsules, spansules, gel caps, solutions, suspensions, syrups, mouthwashes, salves, foams, gels, creams, vaginal bougies and/or suppositones.

17. The method of claim 10 wherein the polymer is present in an amount of about 2 to about 70 parts by weight per part of the complex.

18. The method of claim 10 wherein the glucosamine and the drug are present in the complex in a ratio of about 1 to about 15 moles of glucosamine per mole of the drug.

19. The method of claim 1 wherein the glucosamine having a purity level of at least 99 wt. % and a maximum halide content of about 0.01 wt. % is prepared by the steps of:
   (a) reacting a glucosamine halide with a lithium base in the presence of a $C_1$-$C_4$ alcohol to thereby generate a $C_1$-$C_4$ alcohol solution of a lithium halide and insoluble halide-free glucosamine; and
   (b) separating the insoluble glucosamine from the $C_1$-$C_4$ alcohol solution of the lithium halide.

20. The method of claim 10 wherein the glucosamine having a purity level of at least 99 wt. % and a maximum halide content of about 0.01 wt. % is prepared by the steps of:
   (b) reacting a glucosamine halide with a lithium base in the presence of a $C_1$-$C_4$ alcohol to thereby generate a $C_1$-$C_4$ alcohol solution of a lithium halide and insoluble halide-free glucosamine; and
   (b) separating the insoluble glucosamine from the $C_1$-$C_4$ alcohol solution of the lithium halide.

* * * * *